United States Patent
Conley, Jr. et al.

(10) Patent No.: US 7,309,621 B2
(45) Date of Patent: Dec. 18, 2007

(54) METHOD TO FABRICATE A NANOWIRE CHEMFET SENSOR DEVICE USING SELECTIVE NANOWIRE DEPOSITION

(75) Inventors: John F. Conley, Jr., Camas, WA (US); Yoshi Ono, Camas, WA (US); Lisa H. Stecker, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 328 days.

(21) Appl. No.: 11/115,814

(22) Filed: Apr. 26, 2005

(65) Prior Publication Data

US 2006/0240588 A1  Oct. 26, 2006

(51) Int. Cl.
*H01L 51/40* (2006.01)
*H01L 21/00* (2006.01)
*H01L 21/8238* (2006.01)

(52) U.S. Cl. .......................... 438/99; 438/48; 438/49; 438/200

(58) Field of Classification Search .................. 438/48, 438/49, 21, 22, 99
See application file for complete search history.

(56) References Cited

U.S. PATENT DOCUMENTS

| | | | | |
|---|---|---|---|---|
| 6,914,279 B2* | 7/2005 | Lu et al. | ..................... | 257/252 |
| 7,051,945 B2* | 5/2006 | Empedocles et al. | ....... | 235/492 |
| 2003/0126742 A1* | 7/2003 | Ting et al. | ..................... | 29/874 |
| 2003/0139003 A1* | 7/2003 | Gole et al. | .................. | 438/200 |
| 2005/0064185 A1* | 3/2005 | Buretea et al. | ............. | 428/364 |
| 2005/0070802 A1* | 3/2005 | Peters et al. | ................. | 600/459 |

OTHER PUBLICATIONS

U.S. Appl. No. 10/977,430, filed Oct. 29, 2004, Conley, Jr. et al.
U.S. Appl. No. 10/976,594, filed Oct. 29, 2004, Stecker et al.
U.S. Appl. No. 10/956,786, filed Oct. 1, 2004, Conley, Jr. et al.
Fraden, *Handbook of Modern Sensors*, 2d Ed., AIP Press, p. 499 (1996).
Gordillo et al., *Effect of gas chemisorption on the electrical conductivity of ZnO thin films*, Advances in Mat. Sci. and Tech. 1(1), 1 (1996).
Zhang et al., *Low-temperature growth and Raman scattering study of vertically aligned ZnO nanowires on Si substrates*, APL 83, 4632 (2003).
Martins et al., *Zinc oxide as an ozone sensor*, J. Appl. Phys. 96(3), 1398 (2004).
Eranna et al., *Oxide materials for development of integrated gas sensors—A comprhensive review*, Critical Reviews in Solid State and Materials Sciences 29(3-4): 111-188 (2004).

* cited by examiner

*Primary Examiner*—Scott B. Geyer
*Assistant Examiner*—Seahvosh Nikmanesh
(74) *Attorney, Agent, or Firm*—Law Office of Gerald Maliszewski; Gerald Maliszewski

(57) ABSTRACT

A method of fabricating a nanowire CHEMFET sensor mechanism includes preparing a silicon substrate; depositing a polycrystalline ZnO seed layer on the silicon substrate; patterning and etching the polycrystalline ZnO seed layer; depositing an insulating layer over the polycrystalline ZnO seed layer and the silicon substrate; patterning and etching the insulating layer to form contact holes to a source region and a drain region; metallizing the contact holes to form contacts for the source region and the drain region; depositing a passivation dielectric layer over the insulating layer and the contacts; patterning the passivation layer and etching to expose the polycrystalline ZnO seed layer between the source region and the drain region; and growing ZnO nanostructures on the exposed ZnO seed layer to form a ZnO nanostructure CHEMFET sensor device.

13 Claims, 3 Drawing Sheets

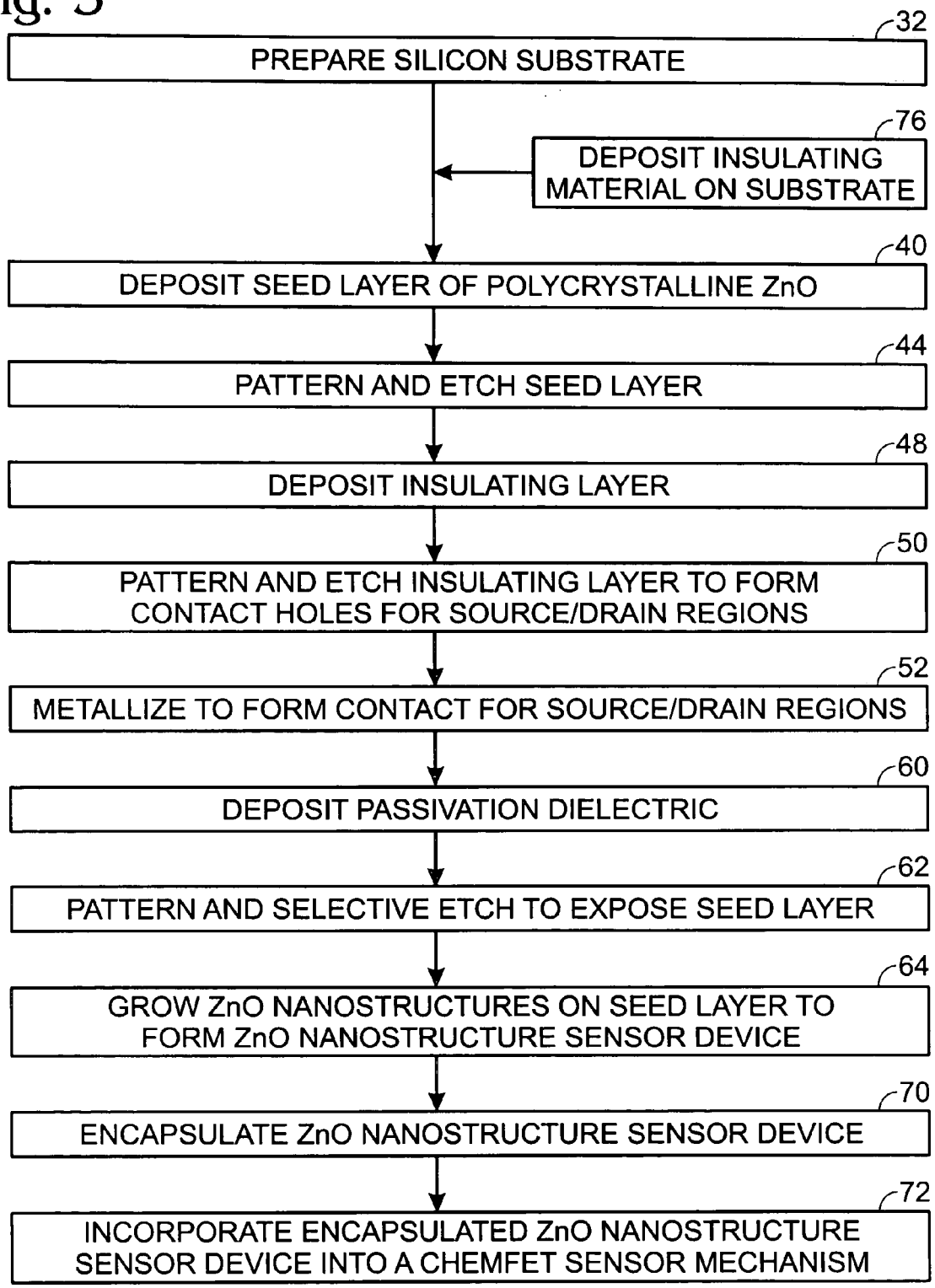

METHOD TO FABRICATE A NANOWIRE CHEMFET SENSOR DEVICE USING SELECTIVE NANOWIRE DEPOSITION

FIELD OF THE INVENTION

This invention relates to nanotechnology and/or microelectronics, solid state sensors/detector, and specifically to a method of fabricating a CHEMFET sensor device using a seed layer on which a collection of nanowires is grown.

BACKGROUND OF THE INVENTION

There is an increasing need for inexpensive sensitive solid state gas sensors for such applications as pollution control, toxic gas monitoring, homeland security, "lab-on-a-chip," etc. It is known that certain materials, such as metal oxides, exhibit sensitivity to various gases due to phenomena at the material surface. Recently, solid state gas sensors have been proposed and fabricated that employ the use of planar thin films of these sensitive materials. Eranna et al., *Oxide materials for development of integrated gas sensors—A comprehensive review*, Critical Reviews in Solid State and Materials Sciences 29 (3-4): 111-188 (2004), describes use of solid state metal oxides as sensors for various gases.

One type of microelectronic sensor device is known as a CHEMFET, as shown in prior art FIGS. 1 and 2, wherein a pH monitor is depicted in FIG. 1, generally at 10, Fraden, *Handbook of Modern Sensors*, 2d Ed., AIP Press, p. 499 (1996). pH monitor 10 includes a CHEMFET sensor device 12, which is encapsulated in a material 14, and works with a reference electrode 16 to determine the pH of a gas. The pH sensor uses silicon dioxide 18 as a gate oxide, which is covered by another gate insulator layer 20, in this case, $Si_3N_4$. A schematic diagram of pH monitor 10 is shown in FIG. 2, in a source-follower mode. These devices are well known and have been used for monitoring quantities, such as pH. The structure of a CHEMFET is similar to that of an MOS transistor in which the gate terminal is replaced by a chemically sensitive film that is left open to the environment. Exposure to gases, liquids, impurities, etc. may modify the surface of the film, changing the surface charge state. The surface field effect modulates charge carrier concentration (conductivity) in the channel. The effect is equivalent to application of a bias to a MOS gate. The current measured between the source and drain terminal is related to the changes in concentration of the substance being sensed. Advantages of this device structure are low power consumption and high sensitivity, which are the results of the FET configuration.

The sensitivity of many known materials, such as $In_2O_3$, $SnO_2$ and ZnO, to various gases has been attributed to surface phenomena. Therefore, nanostructured materials, because of their inherent high surface area, should be ideal for sensing applications. However, a problem has been how to fabricate a useful, i.e., electrically measurable and MOS integratable, device using nanostructured materials.

Martins et al., *Zinc oxide as an ozone sensor*, J. Appl. Phys. 96(3), 1398 (2004), describes the use of a UV bombarded ZnO film-on-glass as a sensor.

Gordillo et al., *Effect of gas chemisorption on the electrical conductivity of ZnO thin films*, Advances in Mat. Sci. and Tech. 1(1), 1 (1996), describes use of an annealed ZnO thin film as a detector for $CO_2$, $O_2$, $H_2$ and $CH_4$.

Zhang et al., *Low-temperature growth and Raman scattering study of vertically aligned ZnO nanowires on Si substrates*, APL 83, 4632 (2003), describes formation of ZnO nanowires on a gold-catalyzed silicon substrate.

SUMMARY OF THE INVENTION

A method of fabricating a nanowire CHEMFET sensor mechanism includes preparing a silicon substrate; depositing a polycrystalline ZnO seed layer on the silicon substrate; patterning and etching the polycrystalline ZnO seed layer; depositing an insulating layer over the polycrystalline ZnO seed layer and the silicon substrate; patterning and etching the insulating layer to form contact holes to a source region and a drain region; metallizing the contact holes to form contacts for the source region and the drain region; depositing a dielectric layer over the insulating layer and the contacts; patterning the dielectric layer and etching to expose the polycrystalline ZnO seed layer between the source region and the drain region; and growing ZnO nanostructures on the exposed ZnO seed layer to form a ZnO nanostructure sensor device. The ZnO nanostructure sensor device may be encapsulated, thus forming a CHEMFET sensor.

It is an object of the invention to provide a method of forming a CHEMFET using nanowires deposited on a sensor gate.

Another object of the invention is to provide a method of growing nanowires using a seed layer of similar material for use in a CHEMFET.

This summary and objectives of the invention are provided to enable quick comprehension of the nature of the invention. A more thorough understanding of the invention may be obtained by reference to the following detailed description of the preferred embodiment of the invention in connection with the drawings.

BRIEF DESCRIPTION OF THE DRAWINGS

FIG. 3 is a block diagram of the method of the invention.

DETAILED DESCRIPTION OF THE PREFERRED EMBODIMENTS

A method for fabricating a CHEMFET sensor having a nanostructured gate material using selective growth of nanowires is described herein, and specifically, growth of ZnO nanowires as an exemplary material. This method will likely work using other appropriate seed layers for other nanowires, such as $In_2O_3$, etc. Selective growth of ZnO nanowires is achieved using a patterned ZnO seed layer as described in U.S. patent application Ser. No. 10/977,430, of Conley, Jr. et al., file Oct. 29, 2004, for Selective growth of ZnO nanowires using a patterned ALD ZnO seed layer. Selective growth of ZnO nanowire bridges is achieved using a patterned ZnO seed layer as described in U.S. patent application Ser. No. 11/152,289 of Conley, Jr. et al., filed Jun. 13, 2005, for Nanowire Sensor Device Structures. These methods are compatible with standard microelectronic processing techniques and may be integrated with CMOS devices.

Figure 1:
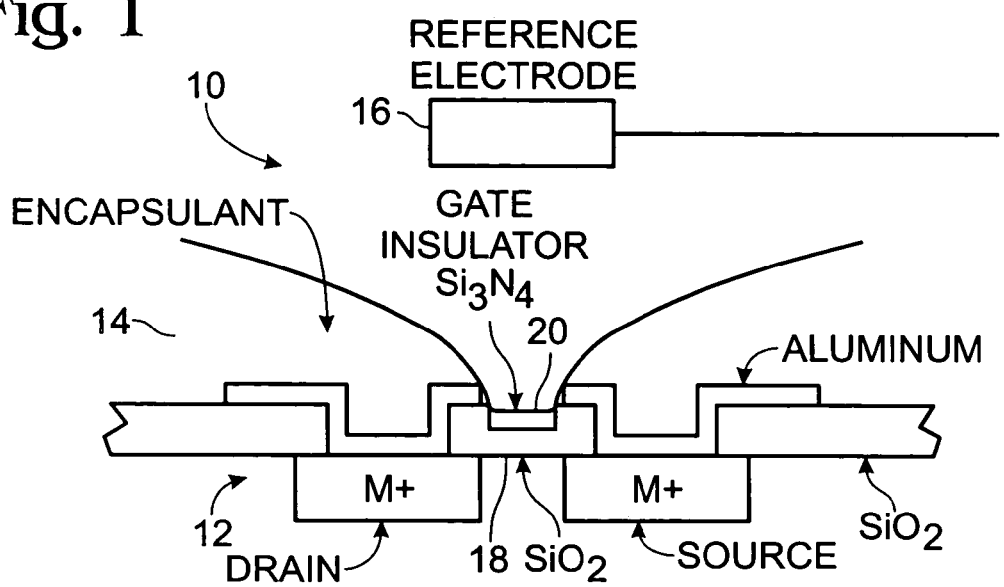
FIG. 1 depicts a prior art CHEMFET intended for use as a pH monitor.
Figure 2:
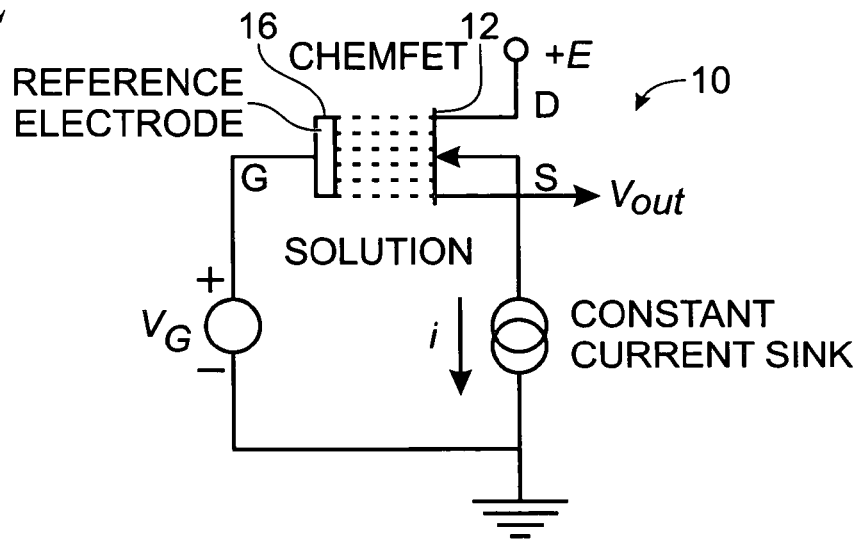
FIG. 2 depicts a schematic of the prior art CHEMFET of FIG. 1.
Figure 4:
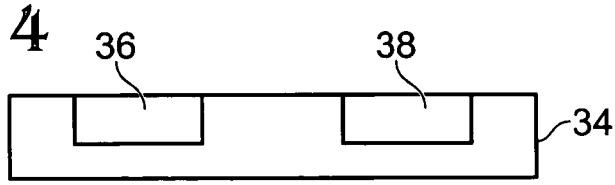
FIGS. 4-8 depict various stages of a CHEMFET constructed according to a first embodiment of the method of the invention.

The method of the invention includes fabricating a CHEMFET sensor using a nanostructured gate material. Referring now to FIGS. 3 and 4, fabrication of the sensor, according to the method of the invention 30, begins by preparing 32 a silicon substrate 34, which includes forming two doped wells 36, 38, of the same type, either n+ or p+, which will become a source region and a drain region, respectively.

Figure 5:
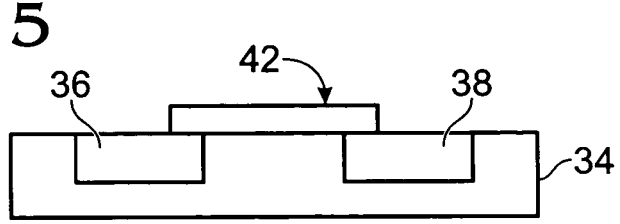

Deposition 40 of a thin film of poly-crystalline ZnO 42 on the surface of the wafer, using a state-of-the-art deposition process, including atomic layer deposition (ALD), spin on deposition, RF sputtering, spray pyrolysis, etc., provides a growth base, or seed layer, for the nanowires to be formed later in the method of the invention. As was previously described in U.S. patent application Ser. No. 10/976,594, of Stecker et al., filed Oct. 29, 2004, for ALD ZnO Seed Layer for Deposition of ZnO nanostructures on a Si substrate, a ZnO film may be used as a seed layer for ZnO nanostructure growth. Any thickness of ZnO between about 1 nm to 100 nm may be used. The choice of thickness may impact the output characteristics of the device, by affecting the capacitance of the gate, depending on the conductivity of the ZnO. This layer is then lithographically patterned and etched 44 to arrive at the structure depicted in FIG. 5.

Figure 6:
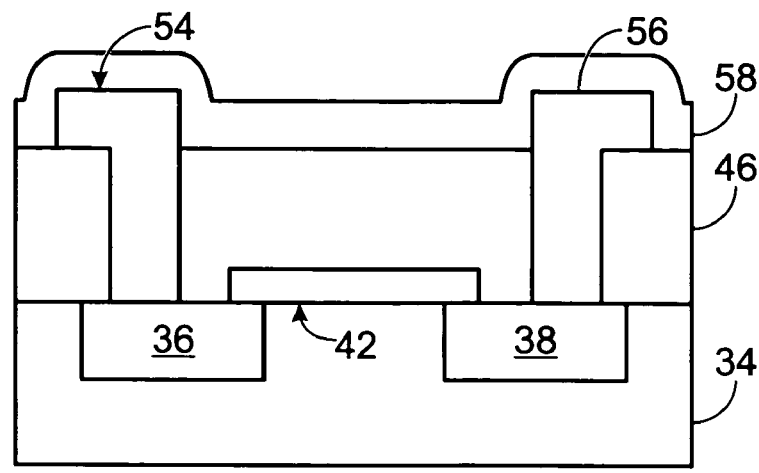
Figure 7:
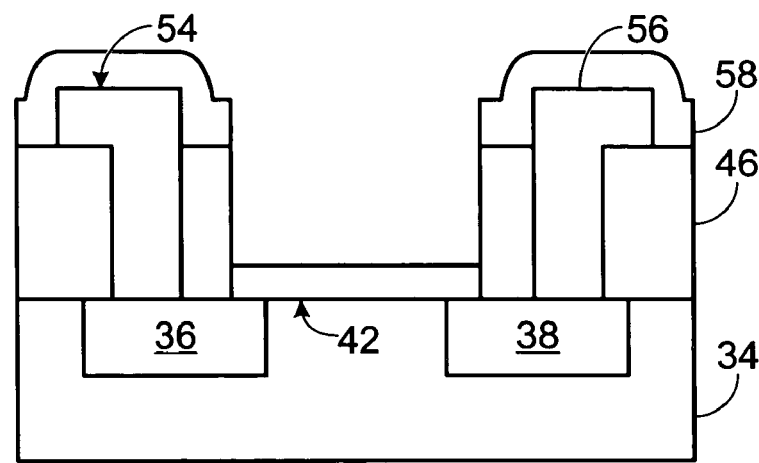

Next, a layer of insulating material 46, such as $SiO_2$, is deposited 48, followed by patterning of contact holes and etching of oxide 46 to form electrical contact holes to the source and drain terminals of the device. The contact holes are filled with a layer of metal, such as aluminum, followed by patterning then etching 52 to form contacts 54, 56. A dielectric layer 58, also referred to herein as a passivation layer, is deposited 60 to produce the structure shown in FIG. 6. The device is patterned and selectively etched 62 to expose ZnO seed layer 42, as shown in FIG. 7.

Figure 8:
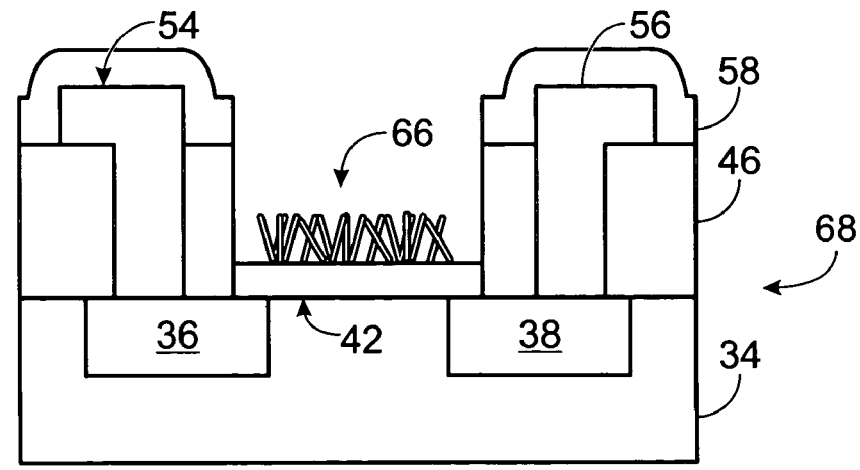

Next, ZnO nanostructure growth 64 is induced. The structure in FIG. 7 is exposed to Zn vapor in the presence of a trace amount of oxygen at temperatures below the melting temperature of the contact metal. Growth takes place via a vapor-solid mechanism only on the ALD ZnO seed layer, as previously disclosed, leaving a nanostructured gate electrode 66, as shown in FIG. 8, which is the ZnO nanostructure sensor device 68 of the method of the invention.

One method for generation of Zn vapor is through carbothermal reduction of ZnO powder using equal parts ZnO and graphite. However, this requires temperatures greater than about 885° C., and therefore requires that the wafer would have to be downstream at a lower temperature. Another method of supplying Zn vapor has been performed at temperatures as low as 450° C. by evaporating Zn powder, as described by Yhang et al., supra. This method may be used in the same chamber. In principal, any method of supplying gas phase Zn for growing would work similarly.

It is anticipated that the device will work similar to CHEMFET devices in that exposure to gases will modify the surface of the ZnO so as to change the surface charge of the wires, which in turn modulates the conductivity of the device channel. Changes in conductivity are measured between source and drain and can be empirically tied to changes in gas concentration. Because of the greatly increased surface area of the nanostructures, this device should be much more sensitive than a planar device.

To complete a CHEMFET sensing mechanism according to the method of the invention, sensor device 68 is encapsulated 70 in a suitable material. Other standard components of the CHEMFET sensor mechanism, such as a resistive heater, p-n junction temperature sensor, etc., are formed by state-of-the-art methods.

In an alternative embodiment, depicted in FIG. 9, a layer of $SiO_2$ 74, or other insulating material may be deposited on silicon substrate 34 before deposition 40 of ZnO seed layer 42.

In an alternative fabrication flow, a replacement gate type process can be used where a nitride or polysilicon dummy gate is formed and occupies the space that will be later filled with ZnO. This method allows high temperature processing for self-aligned source and drain regions with respect to the gate. After implant anneal, multiple layers of dielectric and metallization can be made to form the multi-level interconnects. At the final stage, the channel can be opened to the dummy gate. The dummy gate is removed with a selective etch, whereupon the ALD ZnO and the ZnO nanorods are deposited.

Thus, a method to fabricate a nanowire CHEMFET sensor mechanism using selective nanowire deposition has been disclosed. It will be appreciated that further variations and modifications thereof may be made within the scope of the invention as defined in the appended claims.

We claim:

1. A method of fabricating a nanowire CHEMFET sensor mechanism, comprising:
    preparing a silicon substrate;
    depositing a polycrystalline ZnO seed layer on the silicon substrate;
    patterning and etching the polycrystalline ZnO seed layer;
    depositing an insulating layer over the polycrystalline ZnO seed layer and the silicon substrate;
    patterning and etching the insulating layer to form contact holes to a source region and a drain region;
    metallizing the contact holes to form contacts for the source region and the drain region;
    depositing a passivation dielectric layer over the insulating layer and the contacts;
    patterning the passivation layer and etching to expose the polycrystalline ZnO seed layer between the source region and the drain region; and
    growing ZnO nanostructures on the exposed ZnO seed layer to form a ZnO nanostructure sensor device with an exposed ZnO nanostructure gate electrode.

2. The method of claim 1 which further includes encapsulating the ZnO nanostructure sensor device and incorporating the encapsulated ZnO nanostructure sensor device into a CHEMFET sensor mechanism.

3. The method of claim 1 wherein said depositing a polycrystalline ZnO seed layer on the silicon substrate includes depositing a polycrystalline ZnO seed layer on the silicon substrate by a deposition method taken from the group of methods consisting of atomic layer deposition, spin on depositing, RF sputtering and spray pyrolysis.

4. The method of claim 1 wherein said depositing a polycrystalline ZnO seed layer on the silicon substrate includes depositing a polycrystalline ZnO seed layer on the silicon substrate to a thickness of between about 1 nm and 100 nm.

5. The method of claim 1 wherein said growing ZnO nanostructures on the exposed ZnO seed layer includes selectively growing ZnO nanostructures by vapor-solid deposition by exposing the ZnO seed layer to Zn vapor in the presence of a trace amount of oxygen at temperatures below the melting temperature of a contact metal.

6. A method of fabricating a nanowire CHEMFET sensor mechanism, comprising:
    preparing a silicon substrate, including forming a source region and a drain region;

depositing a polycrystalline ZnO seed layer on the silicon substrate;

patterning and etching the polycrystalline ZnO seed layer;

depositing an insulating layer of silicon oxide over the polycrystalline ZnO seed layer and the silicon substrate;

patterning and etching the silicon oxide layer to form contact holes to the source region and the drain region;

metallizing the contact holes to form contacts for the source region and the drain region;

depositing a passivation dielectric layer over the insulating layer and the contacts;

patterning the passivation layer and etching to expose the polycrystalline ZnO seed layer between the source region and the drain region;

growing ZnO nanostructures on the exposed ZnO seed layer to form a ZnO nanostructure sensor device with an exposed ZnO nanostructure gate electrode;

encapsulating the ZnO nanostructure sensor device; and incorporating the encapsulated ZnO nanostructure sensor device into a CHEMFET sensor mechanism.

7. The method of claim 6 wherein said depositing a polycrystalline ZnO seed layer on the silicon substrate includes depositing a polycrystalline ZnO seed layer on the silicon substrate by a deposition method taken from the group of methods consisting of atomic layer deposition, spin on depositing, RF sputtering and spray pyrolysis.

8. The method of claim 6 wherein said depositing a polycrystalline ZnO seed layer on the silicon substrate includes depositing a polycrystalline ZnO seed layer on the silicon substrate to a thickness of between about 1 nm and 100 nm.

9. The method of claim 6 wherein said growing ZnO nanostructures on the exposed ZnO seed layer includes selectively growing ZnO nanostructures by vapor-solid deposition by exposing the ZnO seed layer to Zn vapor in the presence of a trace amount of oxygen at temperatures below the melting temperature of a contact metal.

10. A method of fabricating a nanowire CHEMFET sensor mechanism, comprising;

preparing a silicon substrate;

depositing a polycrystalline ZnO seed layer on the silicon substrate;

patterning and etching the polycrystalline ZnO seed layer;

depositing an insulating layer over the polycrystalline ZnO seed layer and the silicon substrate;

patterning and etching the insulating layer to form contact holes to a source region and a drain region;

metallizing the contact holes with a contact metal to form contacts for the source region and the drain region;

depositing a passivation dielectric layer over the insulating layer and the contacts;

patterning the passivation layer and etching to expose the polycrystalline ZnO seed layer between the source region and the drain region; and growing ZnO nanostructures on the exposed ZnO seed layer to form a ZnO nanostructure sensor device with an exposed ZnO nanostructure gate electrode, including selectively growing ZnO nanostructures by vapor-solid deposition by exposing the ZnO seed layer to Zn vapor in the presence of a trace amount of oxygen at temperatures below the melting temperature of the contact metal.

11. The method of claim 10 which further includes encapsulating the ZnO nanostructure sensor device and incorporating the encapsulated ZnO nanostructure sensor device into a CHEMFET sensor mechanism.

12. The method of claim 10 wherein said depositing a polycrystalline ZnO seed layer on the silicon substrate includes depositing a polycrystalline ZnO seed layer on the silicon substrate by a deposition method taken from the group of methods consisting of atomic layer deposition, spin on depositing, RF sputtering and spray pyrolysis.

13. The method of claim 10 wherein said depositing a polycrystalline ZnO seed layer on the silicon substrate includes depositing a polycrystalline ZnO seed layer on the silicon substrate to a thickness of between about 1 nm and 100 nm.

* * * * *